United States Patent [19]

Park et al.

[11] Patent Number: 5,051,505

[45] Date of Patent: Sep. 24, 1991

[54] PROCESS FOR PREPARING PIPERAZINYL QUINOLONE DERIVATIVES

[75] Inventors: Sang W. Park; You S. Kim; Jin H. Lee, all of Seoul, Rep. of Korea

[73] Assignee: Korea Institute of Science and Technology, Seoul, Rep. of Korea

[21] Appl. No.: 561,811

[22] Filed: Aug. 2, 1990

[30] Foreign Application Priority Data

Mar. 27, 1990 [KR] Rep. of Korea ............ 4115/1990[U]

[51] Int. Cl.$^5$ .................. C07D 413/14; C07D 401/04
[52] U.S. Cl. ...................................... 544/101; 544/363
[58] Field of Search ............................... 544/363, 101

[56] References Cited

U.S. PATENT DOCUMENTS 4,460,587 7/1984 Vlattas ................................ 514/220

OTHER PUBLICATIONS

Vlattas, "Chemical Abstracts", vol. 101, 1984, Col. 101:211186g.

Primary Examiner—C. Warren Ivy
Assistant Examiner—James H. Turnipseed
Attorney, Agent, or Firm—Cushman, Darby & Cushman

[57] ABSTRACT

A novel process for preparing piperazinyl quinolone derivatives of the formula (I) is disclosed. The process comprises reacting dihaloquinolones with piperazine derivatives and tetraalkyl ammonium halides in the presence of a polar solvent such as acetonitrile, dimethylformamide, pyridine, sulfolane and dimethyl sulfoxide.

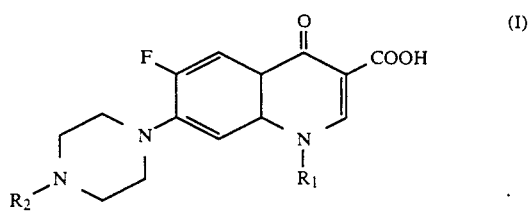

(I)

2 Claims, No Drawings

PROCESS FOR PREPARING PIPERAZINYL QUINOLONE DERIVATIVES

TECHNICAL FIELD

The present invention relates to a novel process for preparing piperazinyl quinolone derivatives represented by the formula (I):

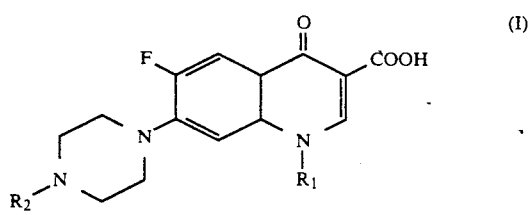

wherein $R_1$ represents $C_{1-6}$ lower alkyl such as methyl, ethyl and cyclopropyl, or 3-oxo-2-propanyl

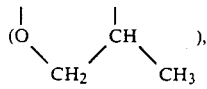

provided that oxygen atom in 3-oxo-2-propanyl is added to the position 8 in quinolone of the formula (I) to form a cyclic compound as follows, and $R_2$ is independently hydrogen or lower alkyl such as methyl and ethyl.

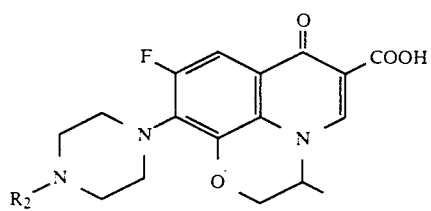

BACKGROUND OF THE INVENTION

In recent years, researches have been conducted on quinolone derivatives of the formula (I) which have a wide spectrum of applications as a fungicide.

Korean Patent Publication No. 87-895 discloses a process for preparing quinolone derivatives of the formula (I) by heating under reflux a dihaloquinolone of the formula (II) in the presence of dry piperazine and dimethyl sulfoxide (DMSO) at 135° C. to 140° C.

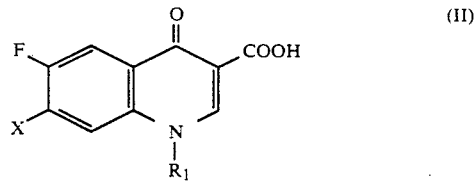

in which $R_1$ is the same as defined for $R_1$ in the formula (I) and X represents halogen.

Alternatively, Korean Patent Publication No. 87-1944 discloses a process for preparing such compounds which comprises heating with stirring a dihaloquinolone in the presence of dry piperazine at 115° C. for 5 hours.

The prior arts heretofore mentioned require elevated reaction temperatures and long reaction time, providing a great deal of energy consumed while they employ solvents of high boiling point only to fail a successful solvent recovery. In addition, time consuming reaction at elevated temperature would cause undesirable by-products which eventually give low yield of the product.

SUMMARY OF THE INVENTION

It is an object of the present invention to provide a novel process for preparing quinolone derivatives of the formula (I) which comprises reacting dihaloquinolones of the formula (II) with piperazine derivatives of the formula (III) and tetraalkyl ammonium halides of the formula (IV) in the presence of a polar solvent.

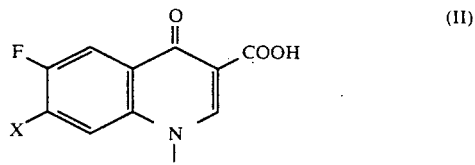

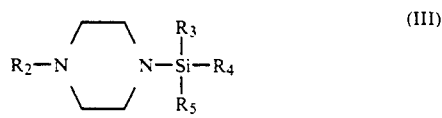

in which $R_1$ is the same as defined for $R_1$ in the formula (1), X represents halogen, $R_2$ is the same as defined for $R_2$ in the formula (I), $R_3$, $R_4$ and $R_5$ are the same or different $C_{1-6}$ lower alkyl selected from a group consisting of methyl, ethyl and t-butyl, and $R_6$ represents methyl, ethyl or butyl.

DETAILED DESCRIPTION OF THE INVENTION

The present inventors have conducted a research to eliminate such defects of the prior arts heretofore mentioned and have found a novel process for preparing piperazinyl quinolone derivatives of the formula (I).

Piperazinyl quinolone derivatives of the formula (I) can be easily prepared by heating with stirring a dihaloquinolone of the formula (II), a piperazine derivative of the formula (III) and a tetraalkyl ammonium halide of the formula (IV) in the presence of a polar solvent such as acetonitrile (AN), dimethylformamide (DMF), pyridine, sulfolane, DMSO and the like at 60° C. to 80° C. for 2 to 3 hours, provided that preferable equivalent ratio of dihaloquinolones of the formula (II) to piperazine derivatives of the formula (III) is 2 to 3 while that of piperazine derivatives of the formula (III) to tetraalkyl ammonium halides of the formula (IV) is 1.0 to 1.2.

Dihaloquinoloes of the formula (II) used in the present invention as a starting material are easily available and can be prepared in accordance with a method known in the literature [J. Med. Chem., 23, 1358 (1980); ibid., 31, 983, 1694 (1988)].

Piperazine derivatives of the formula (III) are novel compounds and can be prepared by stirring piperazine or a 1-alkylpiperazine with a alkylsilyl halide in the presence of methylene chloride at ambient temperature for 12 to 18 hours. Detailed process for preparing such compounds is illustrated in Reference Examples 1 and 2.

Theoretical background of the present invention is based on the fact that a trialkylsilyl group of piperazine derivatives of the formula (III) is cleaved in the presence of a tetraalkyl ammonium halide of the formula (IV) when a silyl atom pushes electrons toward a nitrogen atom of piperazine to increase the nucleophilic reactivity of the piperazine derivatives with the nucleus of quinolone. Increase in nucleophilic reactivity of a silyl atom with aromatic cyclic compounds can be found in the literature [Tetrahedron Lett., Vol. 29, No. 16, 1931 (1988).

Alternative theoretical background is derived from the fact that increase in solubility of quinolone in the presence of tetraammonium ions facilitates the reaction in a solvent such as acetonitrile.

The present invention is illustrated by the following examples. The examples are illustrative only and are not intended to limit the scope of the invention any way. All percentages and ratios are by weight except as otherwise indicated.

EXAMPLE 1

1-Ethyl-6-fluoro-1,4-dihydro-4-oxo-7-(1-piperazinyl)-quinoline-3-carboxylic Acid ($R_1$ Ethyl; $R_2$Hydrogen)

0.5 g (1.85 mmol) of 1-ethyl-6-fluoro-7-chloro-4-oxo1,4-dihydro-quinoline-3-carboxylic acid (II, $R_1$: ethyl; X: chloro) and 1.1 g (5.5 mmol) of 1-(t-butyldimethylsilyl) piperazine ($R_2$: hydrogen, $R_3$ and $R_4$: methyl; $R_5$: t-butyl) are added to 5 ml of pyridine and then heated at 60° C. A solution of 1.73 g (5.5 mmol) of tetrabutyl ammonium fluoride trihydrate in 5 ml of pyridine is added dropwise to the reaction mixture. After completion of addition, the reaction mixture is heated at 80° C. for 2 hours and then distilled under reduced pressure (10 mmHg, 60° C.). The residue is added with water and then stirred to afford a crystal. After filtering and drying, 0.50 g of a solid product is obtained.

Yield: 90.0%.

Melting point: 215° to 217° C.

NMR(CF$_3$COOD)$_{ppm}$: 9.38(1H, s), 8.35(1H, d, J=5H), 7.61 (1H, d, J=8H), 4.96(2H, q), 4.1–4.7(8H, m), 1.85(3H, t).

EXAMPLE 2

1-Ethyl-6-fluoro-1,4-dihydro-4-oxo-7-(4-methyl-piperazinyl)quinoline-3-carboxylic Acid ($R_1$: Ethyl; $R_2$: Methyl)

0.5 g (1.85 mmol) of 1-ethyl-6-fluoro-7-chloro-4-oxo-1,4-dihydro-quinoline-3-carboxylic acid (II, $R_1$: ethyl; X: chloro) and 1.07 g (0.50 mmol) of 4-(t-butyldimethylsilyl)-1-methyl piperazine (III, $R_2$, $R_3$ and $R_4$: methyl; $R_5$: t-butyl) are added to 100 ml of acetonitrile and then heated with stirring. A solution of 1.60 g (0.50 mmol) of tetrabutyl ammonium fluoride trihydrate in 5 ml of acetonitrile is added dropwise to the reaction mixture. After heating with stirring for 3 hours, the solvent is stripped off and water is added thereto to give a solid. After filtering and drying, 0.52 g (85% yield) of a solid compound is afforded.

Melting point: 270° C.

NMR(CF$_3$COOD)$_{ppm}$: 9.35(1H, s), 8.35(1H, d, J=5H), 7.53 (1H, d, J=8H), 4.87(2H, q), 3.55–4.31 (8H, m), 3.25(3H, s), 1.8(3H, t).

EXAMPLE 3

1-Cyclopropyl-6-fluoro-1,4-dihydro 4-oxo-7-[1-piperazinyl)-quinoline-3-carboxylic Acid ($R_1$: Cyclopropyl; $R_2$: Hydrogen)

In a manner similar to that of Example 1, 1-cyclopropyl-6,7-difluoro-4-oxo-1,4-dihydro-quinoline-3-carboxylic acid (II, $R_1$: cyclopropyl; X: fluoro) is reacted with 1-butylmethylsilyl piperazine (III, $R_2$: hydrogen; $R_3$ and $R_4$: methyl; $R_5$: t-butyl) to give a solid compound.

Yield. 95%.

Melting point; 270° C.

NMR(CF$_3$COOD)$_{ppm}$: 9.35(1H, s), 8.29–8.35(1H, d), 7.94–7.98 (1H, d), 4.13(1H, m), 3.83–4.02(8H, m), 1.48–1.73(4H, m).

EXAMPLE 4

1-Cyclopropyl-6-fluoro-1,4-dihydro-4-oxo-7-(1-piperazinyl)-quinoline-3-carboxylic Acid ($R_1$: Cyclopropyl; $R_2$: Hydrogen)

In a manner similar to that of Example 1, 1-cyclopropyl-6-fluoro-7-chloro-1,4-dihydro-4-oxo-quinoline-3-carboxylic acid (II, $R_1$: cyclopropyl; X: chloro) is reacted with 1-(t-butylmethylsilyl)piperazine (III, $R_2$: hydrogen; $R_3$ and $R_4$: methyl; $R_5$: t-butyl) to afford a solid compound.

Yield: 88%.

EXAMPLE 5

9-Fluoro-3-methyl-10-(4-methyl-1-piperazinyl)-7-oxo-2,3-dihydro-7H-pyrido [1,2,3-de]-1,4-Benzoxazin-6-carboxylic Acid ($R_2$: Methyl)

In a manner similar to that of Example 4, 9,10-difluoro-3-methyl-7-oxo-2,3-dihydro-7H-pyrido [1,2,3-de]-1,4-benzoxazin- 6-carboxylic acid (II, X: fluoro) is reacted with 4-(t-butyldimethylsilyl)-1-methylpiperazine (III, $R_2$, $R_3$ and $R_4$: methyl; $R_5$: t-butyl) to obtain a solid compound.

Yield. 94%.

Melting point: 249° to 250° C.

REFERENCE EXAMPLE 1

4-(t-Butylmethylsilyl)-1-methylpiperazine (III, $R_2$, $R_3$ and $R_4$: Methyl; $R_5$: t-Butyl)

10 g (0.1 mol) of 1-methylpiperazine and 11.1 g (0.11 mol) of triethylamine are dissolved in 500 ml of methylene chloride and then the reaction mixture is cooled to 0° C. A solution of 16.6 g (0.11 mol) of t-butyldimethylsilyl chloride in 20 ml of methylene chloride is slowly added to the reaction mixture and stirred at room temperature for 18 hours. The reaction mixture is passed through a silica gel column and the solvent is stripped off under reduced pressure. The residue is distilled under reduced pressure (115° C. to 120° C./0.5 mmHg) to afford 18.4 g of a colorless liquid compound.

Yield: 86%.

NMR(CDCl$_3$)$_{ppm}$: 2.7–2.9(4H, t, J=5H), 2.0–2.2(4H, t), 2.2 (3H, s), 0.8(9H, s), 0.0(6H, s).

REFERENCE EXAMPLE 2

1-(t-Butyldimethylsilyl)piperazine III, $R_2$Hydrogen; $R_3$ and $R_4$: Methyl; $R_5$: t-Butyl)

In a manner similar to that of Reference Example 1, piperazine is reacted with t-butyldimethylsilyl chloride. After distilling under reduced pressure (115° C. to 121° C./0.5 mmHg), a colorless solid compound is obtained.
Yield: 70%.
Melting point: 95° to 98° C.
NMR(CDCl$_3$)$_{ppm}$: 3.1(1H, s), 1.8–2.2(8H, m), 0.1(9H, s), 0.0(6H, s).

REFERENCE EXAMPLE 3

4-(Trimethylsilyl)-1-methylpiperazine (V, $R_2$, $R_3$, $R_4$ and $R_5$: Methyl)

In a manner similar to that of Reference Example 1, 1-methylpiperazine is reacted with trimethylsilyl chloride. After distilling under reduced pressure (75° C. to 80° C./0.5 mmHg), a colorless liquid compound is afforded.
Yield: 87%.
NMR(CDCl$_3$)$_{ppm}$: 2.9–3.2(4H, t), 2.2–2.4(4H, t), 2.3(3H, s), 0.1(9H, s).

What is claimed is:

1. A process for preparing piperazinyl quinolone derivatives of the formula (I):

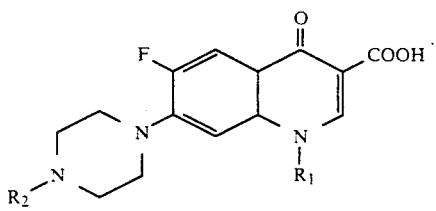

wherein $R_1$ is $C_{1-6}$ lower alkyl cyclopropyl, or 3-oxo-2-propanyl, provided that oxygen atom in 3-oxo-2-propanyl is added to the position 8 is quinolone of the formula (I) to form a cyclic compound, and $R_2$ represents hydrogen, methyl or ethyl, which comprises reacting dihaloquinolones of the formula (II) with piperazine derivatives of the formula (III) in the presence of a polar solvent and a tetraalkyl ammonium halide of the formula (IV) at 60° C. to 80° C. for 2 to 3 hours.

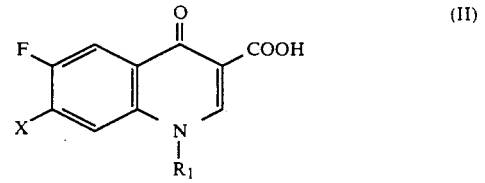

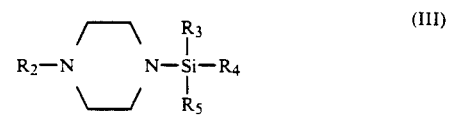

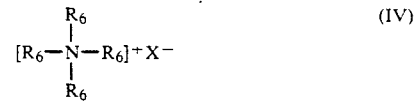

wherein
$R_1$ is the same as defined for $R_1$ in the formula (I),
X represents chloro or fluoro,
$R_2$ is hydrogen, methyl or ethyl,
$R_3$, $R_4$ and $R_5$ are the same or different $C_{1-6}$ lower alkyl groups selected from a group consisting of methyl, ethyl and t-butyl,
$R_6$ is methyl, ethyl or butyl, and
X is chloro or fluoro.

2. A process as claimed in claim 1 wherein a polar solvent is a member selected from a group consisting of acetonitrile, dimethylformamide, pyridine, sulfolane and dimethyl sulfoxide.

* * * * *